(12) United States Patent
Takemoto et al.

(10) Patent No.: US 7,494,763 B2
(45) Date of Patent: Feb. 24, 2009

(54) POLYHYDRIC PHENOL COMPOUND AND CHEMICALLY AMPLIFIED RESIST COMPOSITION CONTAINING THE SAME

(75) Inventors: Ichiki Takemoto, Kawanishi (JP); Nobuo Ando, Toyonaka (JP); Junji Shigematsu, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/976,197

(22) Filed: Oct. 22, 2007

(65) Prior Publication Data

US 2008/0248417 A1    Oct. 9, 2008

(30) Foreign Application Priority Data

Oct. 25, 2006   (JP)   ............... 2006-289737

(51) Int. Cl.
*G03F 7/004* (2006.01)
*C07C 69/74* (2006.01)

(52) U.S. Cl. .................. 430/270.1; 430/905; 430/910; 560/114; 560/116

(58) Field of Classification Search ............... 430/191, 430/192, 193, 270.1, 905, 910; 560/114, 560/116
See application file for complete search history.

(56) References Cited

U.S. PATENT DOCUMENTS

| 5,407,779 | A * | 4/1995 | Uetani et al. | 430/192 |
| 5,866,724 | A | 2/1999 | Ichikawa et al. | |
| 6,492,085 | B1 * | 12/2002 | Shimatani et al. | 430/191 |
| 6,551,755 | B2 * | 4/2003 | Hidesaka et al. | 430/191 |
| 6,869,742 | B2 * | 3/2005 | Mizuta et al. | 430/190 |

FOREIGN PATENT DOCUMENTS

JP    2006-058739 A    3/2006

OTHER PUBLICATIONS

Yamaguchi et al, "Characterization of Line-Edge Roughness in Resist Patterns and Estimation of its Effect on Device Performance," Proceedings of SPIE, vol. 5038 (2003), pp. 689-694.

\* cited by examiner

*Primary Examiner*—John S Chu
(74) *Attorney, Agent, or Firm*—Birch, Stewart, Kolasch & Birch, LLP

(57) ABSTRACT

The present invention provides a polyhydric phenol compound represented by the formula (I):

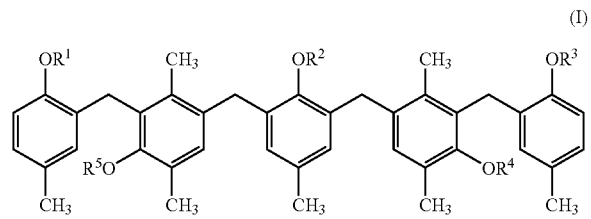

(I)

wherein at least one selected from $R^1$, $R^2$, $R^3$, $R^4$, and $R^5$ is a group represented by the formula (II):

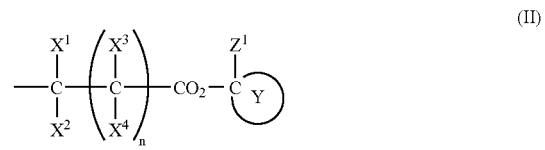

(II)

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group,
and the others are hydrogen atoms, and a chemically amplified resist composition containing the same.

11 Claims, No Drawings

POLYHYDRIC PHENOL COMPOUND AND CHEMICALLY AMPLIFIED RESIST COMPOSITION CONTAINING THE SAME

This nonprovisional application claims priority under 35 U.S.C. § 119(a) on Patent Application No. 2006-289737 filed in JAPAN on Oct. 25, 2006, the entire contents of which are hereby incorporated by reference.

FIELD OF THE INVENTION

The present invention relates to a polyhydric phenol compound and a chemically amplified resist composition containing the same.

BACKGROUND OF THE INVENTION

A chemically amplified resist composition is used for semiconductor microfabrication.

In semiconductor microfabrication, it is desirable to form patterns having high resolution, high sensitivity and good line-edge roughness, and it is expected for a chemically amplified resist composition to give such patterns.

JP 2006-58739A discloses a chemically amplified resist composition containing a polyhydric phenol compound wherein at least one hydroxyl group bonded to a phenyl group is protected by a 1-ethoxyethyl group.

SUMMARY OF THE INVENTION

An object of the present invention is to provide a novel polyhydric phenol compound capable of providing a chemically amplified resist composition giving patterns having good resolution and good line edge roughness.

The other object of the present invention is to provide a chemically amplified resist composition containing the same.

These and other objects of the present invention will be apparent from the following description.

The present invention relates to the followings:

<1> A polyhydric phenol compound represented by the formula (I):

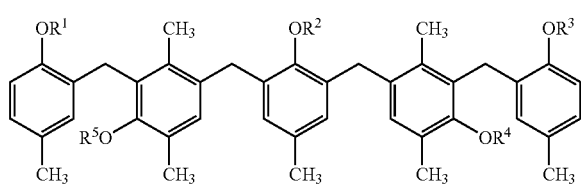

wherein at least one selected from $R^1$, $R^2$, $R^3$, $R^4$, and $R^5$ is a group represented by the formula (II):

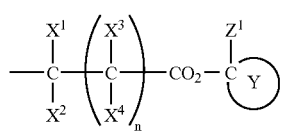

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms;

<2> The polyhydric phenol compound according to <1>, wherein $X^1$ and $X^2$ represent hydrogen atoms and n represents 0;

<3> The polyhydric phenol compound according to <1>, wherein the molecular weight of the polyhydric phenol compound represented by the formula (I) is 730 to 5000;

<4> A chemically amplified resist composition comprising a polyhydric phenol compound represented by the formula (I):

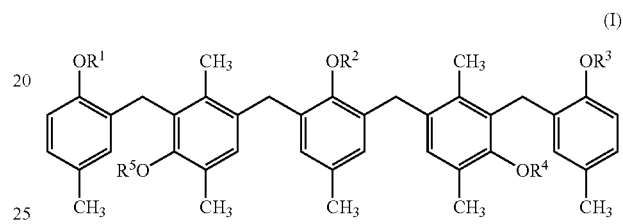

wherein at least one selected from $R^1$, $R^2$, $R^3$, $R^4$, and $R^5$ is a group represented by the formula (II):

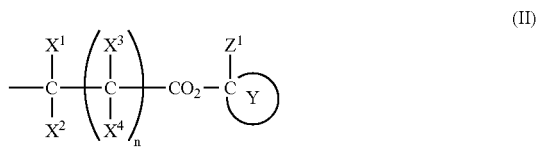

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms, and an acid generator;

<5> The chemically amplified resist composition according to <4>, wherein the composition contains at least two kinds of the polyhydric phenol compound represented by the formula (I);

<6> The chemically amplified resist composition according to <4> or <5>, wherein the composition further contains at least one compound selected from a compound represented by the formula (III):

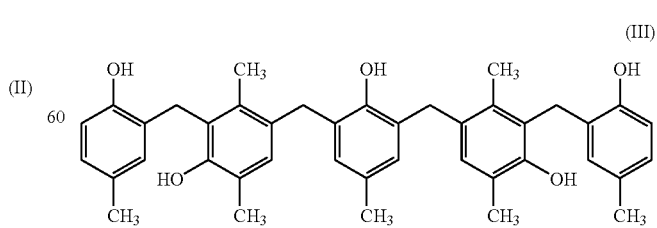

and a compound represented by the formula (V):

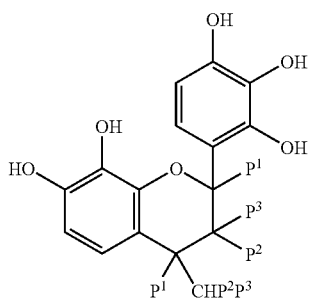

wherein $P^1$, $P^2$ and $P^3$ each independently represents a hydrogen atom, a C1-C4 alkyl group, a C2-C4 alkenyl group, a C3-C8 cycloalkyl group, a C6-C12 aryl group or a C7-C12 aralkyl group;

<7> The chemically amplified resist composition according to <4> or <5>, wherein the composition further contains a resin containing a structural unit which has an acid-labile group and which itself is insoluble or poorly soluble in an aqueous alkali solution but becomes soluble in an aqueous alkali solution by the action of an acid;

<8> The chemically amplified resist composition according to <4> or <5>, wherein the composition further contains a resin containing a structural unit which has an acid-labile group and which itself is insoluble or poorly soluble in an aqueous alkali solution but becomes soluble in an aqueous alkali solution by the action of an acid and at least one compound selected from a compound represented by the formula (III):

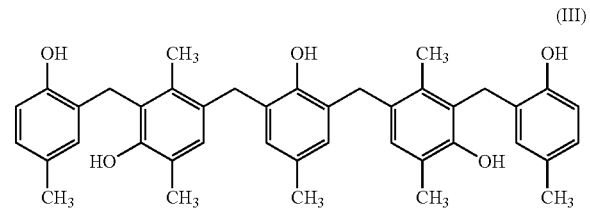

and a compound represented by the formula (V):

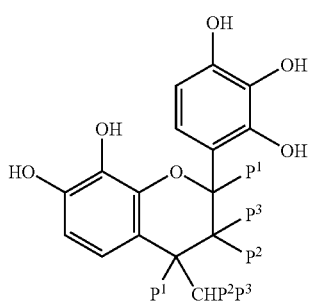

wherein $P^1$, $P^2$ and $P^3$ each independently represents a hydrogen atom, a C1-C4 alkyl group, a C2-C4 alkenyl group, a C3-C8 cycloalkyl group, a C6-C12 aryl group or a C7-C12 aralkyl group;

<9> The chemically amplified resist composition according to <7>, wherein the resin containing a structural unit which has an acid-labile group and which itself is insoluble or poorly soluble in an aqueous alkali solution but becomes soluble in an aqueous alkali solution by the action of an acid is a resin containing a structural unit derived from a 2-alkyl-2-adamantyl acrylate, a 2-alkyl-2-adamantyl methacrylate, a 2-alkyl-2-adamantyl α-chloroacrylate or a 2-alkyl-2-adamantyl α-trifluoromethylacrylate, and a structure unit derived from hydroxystyrene;

<10> The chemically amplified resist composition according to <8>, wherein the resin containing a structural unit which has an acid-labile group and which itself is insoluble or poorly soluble in an aqueous alkali solution but becomes soluble in an aqueous alkali solution by the action of an acid is a resin containing a structural unit derived from a 2-alkyl-2-adamantyl acrylate, a 2-alkyl-2-adamantyl methacrylate, a 2-alkyl-2-adamantyl α-chloroacrylate or a 2-alkyl-2-adamantyl α-trifluoromethylacrylate, and a structure unit derived from hydroxystyrene;

<11> A process for production of a polyhydric phenol compound represented by the formula (I):

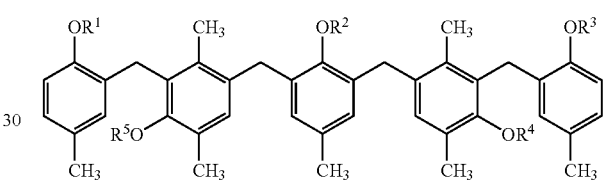

wherein at least one selected from $R^1$, $R^2$, $R^3$, $R^4$, and $R^5$ is a group represented by the formula (II):

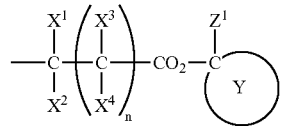

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms, which comprises reacting a compound represented by the formula (III):

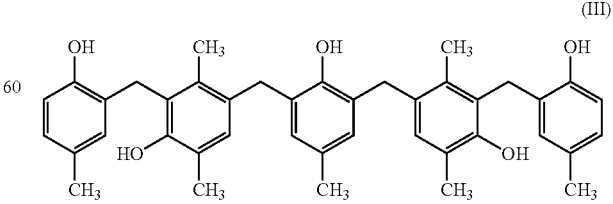

with a compound represented by the formula (IV):

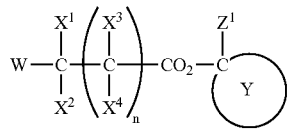

(IV)

wherein $X^1$, $X^2$, $X^3$, $X^4$, n, $Z^1$ and Y are the same as defined above, and W represents a chlorine atom, a bromine atom, an iodine atom, a methanesulfonyloxy group or a p-toluenesulfonyloxy group.

DESCRIPTION OF PREFERRED EMBODIMENTS

First, the present polyhydric phenol compound represented by the formula (I) (hereinafter, simply referred to as the polyhydric phenol compound (I)) will be illustrated.

In the polyhydric phenol compound (I), at least one selected from $R^1$, $R^2$, $R^3$, $R^4$, and $R^5$ is a group represented by the formula (II):

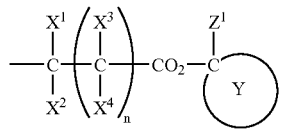

(II)

(hereinafter, simply referred to as the group (II)) and the others are hydrogen atoms.

In the group (II), $X^1$, $X^2$, $X^3$ and $X^4$ each independently represent a hydrogen atom or a C1-C4 alkyl group. Examples of the C1-C4 alkyl group include a methyl, ethyl, n-propyl, isopropyl, n-butyl, isobutyl, sec-butyl and tert-butyl group. It is preferred that $X^1$, $X^2$, $X^3$ and $X^4$ each independently represent the hydrogen atom, the methyl group or the ethyl group. It is more preferred that $X^1$, $X^2$, $X^3$ and $X^4$ are the same and represent hydrogen atoms, methyl groups or ethyl groups, and it is especially preferred that $X^1$, $X^2$, $X^3$ and $X^4$ are the same and represent hydrogen atoms.

In the group (II), n represents an integer of 0 to 3, preferably an integer of 0 or 1, and more preferably 0.

$Z^1$ represents a C1-C6 alkyl group or a C3-C12 cycloalkyl group, and the C1-C6 alkyl group is preferable. Examples of the C1-C6 alkyl group include a methyl, ethyl, n-propyl, isopropyl, n-butyl, isobutyl, sec-butyl, tert-butyl, n-pentyl, 3-methylbutyl and n-hexyl group, and the methyl, ethyl and isopropyl group are preferable. Examples of the C3-C12 cycloalkyl group include a cyclopropyl, cyclobutyl, cyclopentyl, cyclohexyl, cycloheptyl and cyclooctyl group.

The ring Y represents an alicyclic hydrocarbon group. The alicyclic hydrocarbon group may have monocycle or bicycle or more, and the alicyclic hydrocarbon group having bicycle or more is preferable.

Examples of the alicyclic hydrocarbon group include the followings.

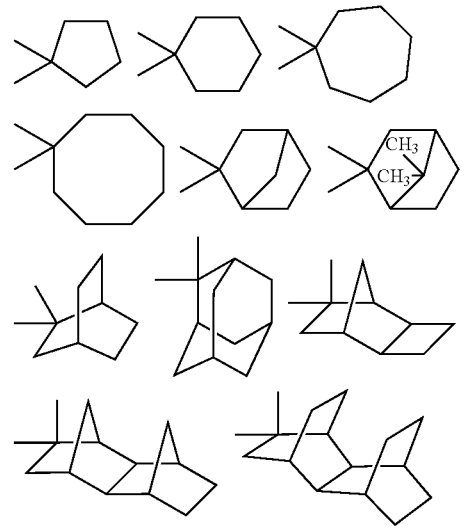

In the above formulae, one straight line with an open end shows a bond extended from the adjacent —$CO_2$—, and the other straight line with an open end shows a bond extended from the adjacent group $Z^1$.

Preferable examples thereof include the followings:

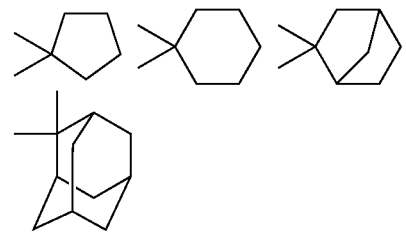

and more preferable examples thereof include the followings:

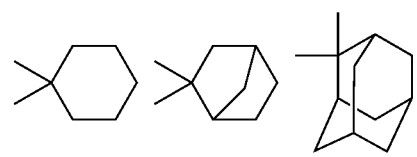

and especially preferable examples thereof include the followings:

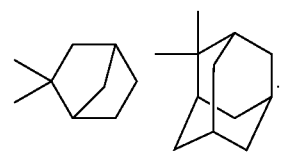

In the above formulae, one straight line with an open end shows a bond extended from the adjacent —CO$_2$—, and the other straight line with an open end shows a bond extended from the adjacent group Z$^1$.
As the group represented by the following formula:
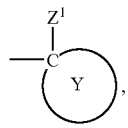
following groups are exemplified.
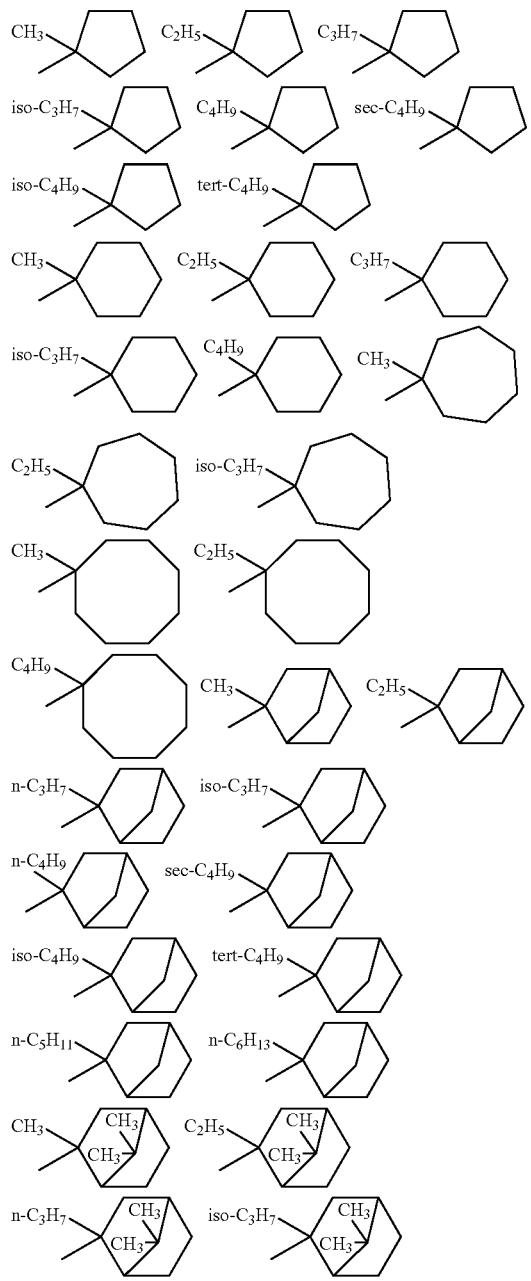
-continued
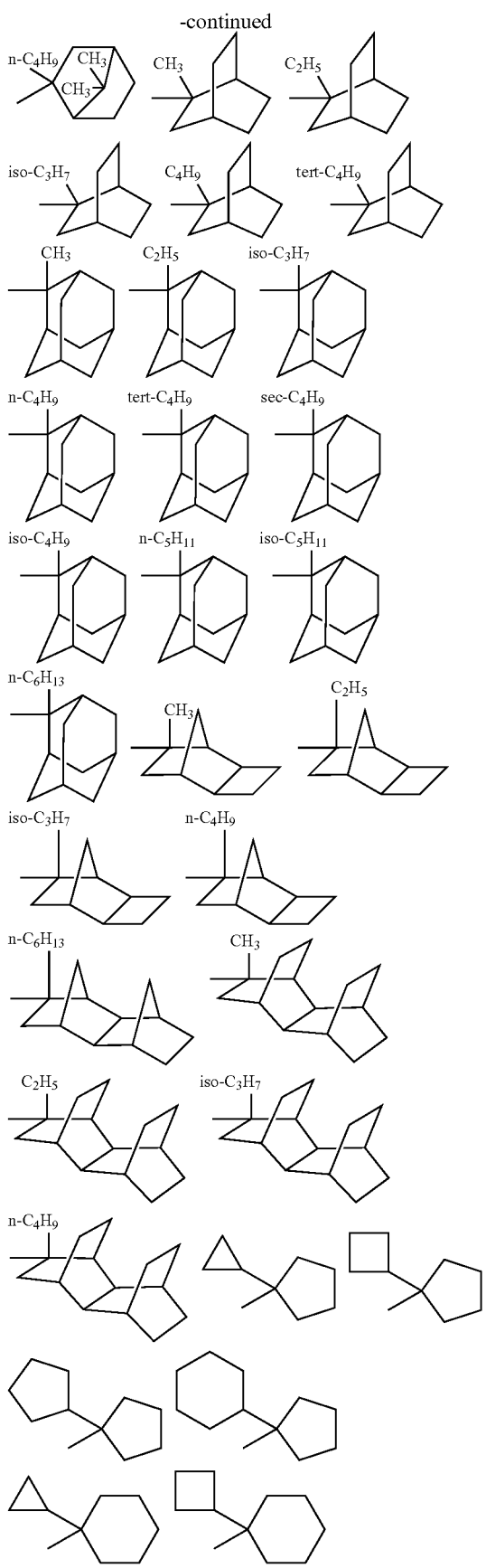

-continued

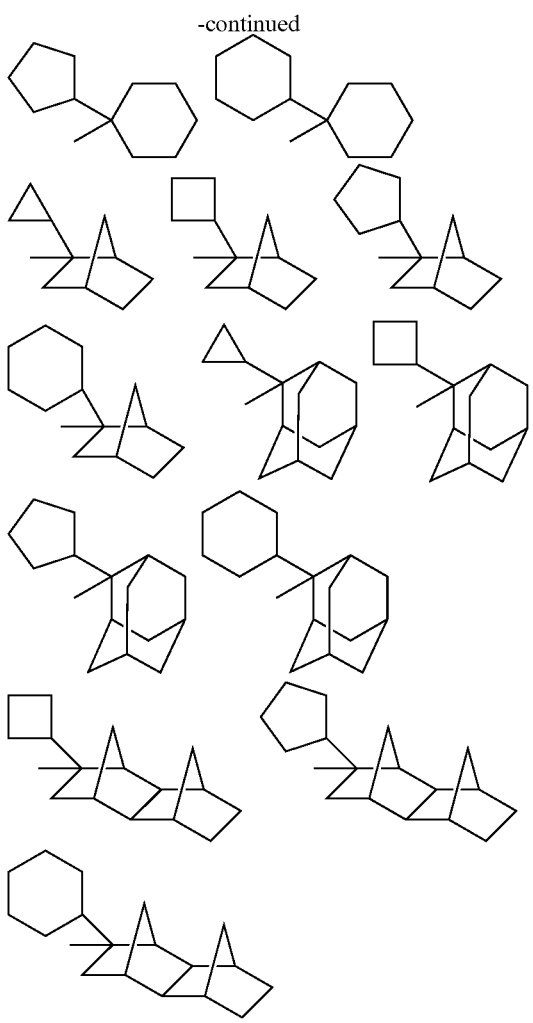

In the above formulae, a straight line with an open end shows a bond extended from the adjacent —CO$_2$—.

Preferable examples thereof include

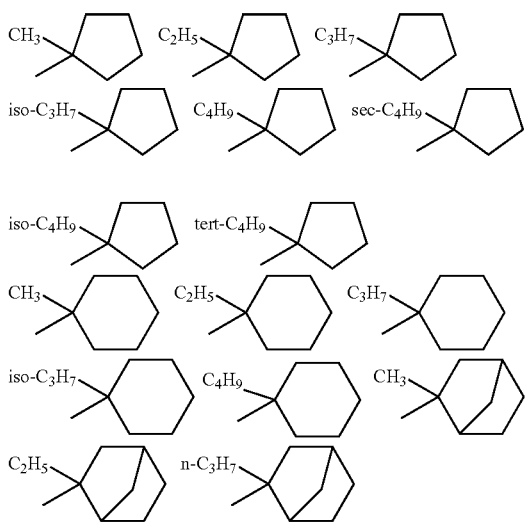

-continued

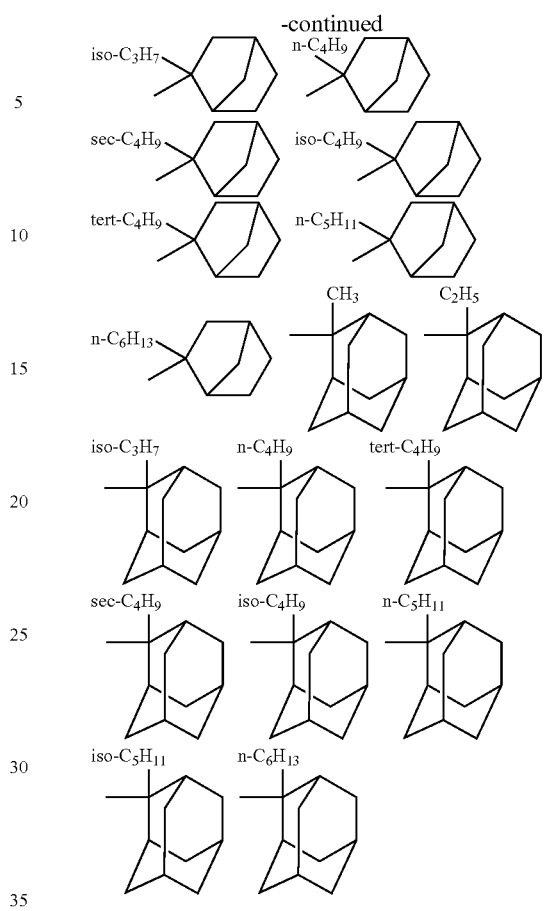

In the above formulae, a straight line with an open end shows a bond extended from the adjacent —CO$_2$—.

It is preferred that the group (II) is the following.

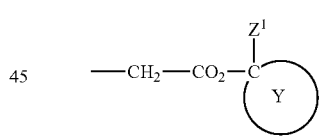

Examples of the polyhydric phenol compound (I) include the polyhydric phenol compound wherein any one of $R^1$, $R^2$, $R^3$, $R^4$, and $R^5$ is the group (II) and the other four groups are hydrogen atoms; the polyhydric phenol compound wherein any two of $R^1$, $R^2$, $R^3$, $R^4$, and $R^5$ are the groups (II) and the other three groups are hydrogen atoms; the polyhydric phenol compound wherein any three of $R^1$, $R^2$, $R^3$, $R^4$, and $R^5$ are the groups (II) and the other two groups are hydrogen atoms; the polyhydric phenol compound wherein any four of $R^1$, $R^2$, $R^3$, $R^4$, and $R^5$ are groups (II) and the other group is a hydrogen atom; and the polyhydric phenol compound wherein all of $R^1$, $R^2$, $R^3$, $R^4$, and $R^5$ are the groups (II).

Preferred are the polyhydric phenol compound (I) wherein any one of $R^1$, $R^2$, $R^3$, $R^4$, and $R^5$ is the group (II) and the other four groups are hydrogen atoms; the polyhydric phenol compound (I) wherein any two of $R^1$, $R^2$, $R^3$, $R^4$, and $R^5$ are the groups (II) and the other three groups are hydrogen atoms;

and the polyhydric phenol compound (I) wherein any three of $R^1$, $R^2$, $R^3$, $R^4$, and $R^5$ are the groups (II) and the other two groups are hydrogen atoms.

The molecular weight of the polyhydric phenol compound (I) is usually 730 to 5000.

The polyhydric phenol compound (I) can be produced by a reaction of a compound represented by the formula (III):

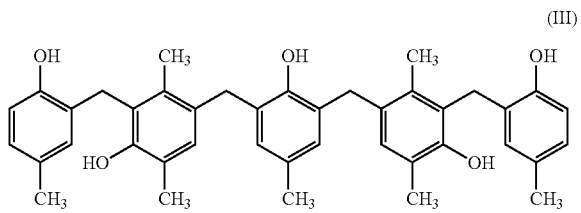

(hereinafter, simply referred to as the compound (III)) and a compound represented by the formula (IV):

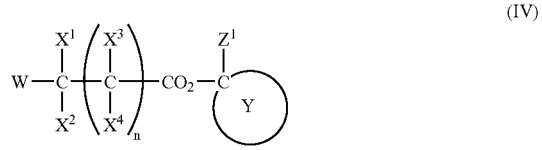

wherein $X^1$, $X^2$, $X^3$, $X^4$, n, $Z^1$ and Y are the same as defined above, and W represents a chlorine atom, a bromine atom, an iodine atom, a methanesulfonyloxy group or a p-toluenesulfonyloxy group (hereinafter, simply referred to as the compound (IV)).

The compound (III) can be produced according to the method described in U.S. Pat. No. 5,866,724 A.

As the compound (IV), commercially available one may be used and one produced by a known method may be used.

The reaction of the compound (III) and the compound (IV) is usually conducted in an inert solvent such as toluene, tetrahydrofuran, N,N-dimethylformamide and dimethylsulfoxide. The reaction temperature is usually −30 to 200° C., preferably 0 to 150° C.

The amount of the compound (IV) to be used is usually 1 to 6 moles, and preferably 1 to 4 moles relative to 1 mole of the compound (III).

The reaction is preferably conducted in the presence of a base. Examples of the base include an organic base such as triethylamine, pyridine, sodium methoxide, sodium ethoxide and potassium tert-butoxide; an inorganic base such as sodium hydride, potassium carbonate and sodium hydroxide. These bases may be used alone and a mixture thereof may be used. The amount of the base is usually 1 to 6 moles, and preferably 1 to 4 moles relative to 1 mole of the compound (III).

The reaction may be conducted in the presence of a phase transfer catalyst such as tetrabutylammonium bromide. The reaction may also be conducted in the presence of an iodide compound such as potassium iodide.

After completion of the reaction, the polyhydric phenol compound (I) can be isolated, for example, by conducting extraction treatment of the reaction mixture and then concentrating the organic layer obtained. The polyhydric phenol compound (I) isolated may be further purified by a conventional purification means such as column chromatography, recrystallization and distillation.

Next, the present chemically amplified resist composition will be illustrated.

The polyhydric phenol compound (I) itself is insoluble or poorly soluble in an aqueous alkali solution and becomes soluble in an aqueous alkali solution by the action of an acid.

The present chemically amplified resist composition contains the polyhydric phenol compound (I) and an acid generator.

The acid generator generates an acid with the action of radiation, and the acid generated by irradiation to the present resist composition catalytically acts against the polyhydric phenol compound (I), cleaves the group capable of being cleaved by the acid, and the polyhydric phenol compound (I) becomes soluble in an alkali aqueous solution.

The present resist composition preferably contains at least two kinds of the polyhydric phenol compound (I). The present resist composition preferably contains the polyhydric phenol compound (I) wherein any two of $R^1$, $R^2$, $R^3$, $R^4$, and $R^5$ are the groups (II) and the other three groups are hydrogen atoms.

The resist composition containing the polyhydric phenol compound (I) wherein any one of $R^1$, $R^2$, $R^3$, $R^4$, and $R^5$ is the group (II) and the other four groups are hydrogen atoms and the polyhydric phenol compound (I) wherein any two of $R^1$, $R^2$, $R^3$, $R^4$, and $R^5$ are the groups (II) and the other three groups are hydrogen atoms;

the resist composition containing the polyhydric phenol compound (I) wherein any one of $R^1$, $R^2$, $R^3$, $R^4$, and $R^5$ is the group (II) and the other four groups are hydrogen atoms, the polyhydric phenol compound (I) wherein any two of $R^1$, $R^2$, $R^3$, $R^4$, and $R^5$ are the groups (II) and the other three groups are hydrogen atoms and the polyhydric phenol compound (I) wherein any three of $R^1$, $R^2$, $R^3$, $R^4$, and $R^5$ are the groups (II) and the other two groups are hydrogen atoms; and the resist composition containing the polyhydric phenol compound (I) wherein any two of $R^1$, $R^2$, $R^3$, $R^4$, and $R^5$ are the groups (II) and the other three groups are hydrogen atoms and the polyhydric phenol compound (I) wherein any three of $R^1$, $R^2$, $R^3$, $R^4$, and $R^5$ are the groups (II) and the other two groups are hydrogen atoms, are preferable.

The acid generator in the resist composition of the present invention can be selected from various compounds generating an acid by irradiation with radiation on the acid generator itself or a resist composition containing the acid generator. For example, an onium salt, a halogenated alkyltriazine compound, a disulfone compound, a diazomethane compound having a sulfonyl group, a sulfonate compound and an imide compound having a sulfonyloxy group, are exemplified.

As the onium salt, an onium salt in which one or more nitro groups are contained in an anion, an onium salt in which one or more ester groups are contained in an anion, and the like are listed.

Examples of the onium salt include diphenyliodonium trifluoromethanesulfonate, (4-methoxyphenyl)phenyliodonium hexafluoroantimonate, (4-methoxyphenyl)phenyliodonium trifluoromethanesulfonate, bis(4-tert-butylphenyl)iodonium tetrafluoroborate, bis(4-tert-butylphenyl)iodonium hexafluorophosphate, bis(4-tert-butylphenyl)iodonium hexafluoroantimonate, bis(4-tert-butylphenyl)iodonium trifluoromethanesulfonate, triphenylsulfonium hexafluorophosphate, triphenylsulfonium hexafluoroantimonate, triphenylsulfonium (1-adamantylmethoxy)carbonyldifluoromethanesulfonate, triphenylsulfonium (3-hydroxymethyl-1-adamantyl)methoxycarbonyldifluoromethanesulfonate, triphenylsulfonium 1-(hexahydro-2- oxo-3,5-methano-2H-cyclopenta[b]furan-6-yloxycarbonyl)
difluoromethanesulfonate, triphenylsulfonium (4-oxo-1-
adamantyloxy)carbonyldifluoromethanesulfonate,
triphenylsulfonium (3-hydroxy-1-adamantyl)methoxycar-
bonyldifluoromethanesulfonate, (4-methylphenyl)diphenyl-
sulfonium nonafluorobutanesulfonate, (4-methoxyphenyl)
diphenylsulfonium hexafluoroantimonate,
(4-methoxyphenyl)diphenylsulfonium trifluoromethane-
sulfonate, (4-methylphenyl)diphenylsulfonium trifluo-
romethanesulfonate, (4-methylphenyl)diphenylsulfonium
heptadecafluorooctanesulfonate, (2,4,6-trimethylphenyl)
diphenylsulfonium trifluoromethanesulfonate, (4-tert-bu-
tylphenyl)diphenylsulfonium trifluoromethanesulfonate,
(4-phenylthiophenyl)diphenylsulfonium hexafluorophos-
phate, (4-phenylthiophenyl)diphenylsulfonium hexafluoro-
antimonate, 1-(2-naphthoylmethyl)thiolanium hexafluoro-
antimonate, 1-(2-naphthoylmethyl)thiolanium
trifluoromethanesulfonate, (4-hydroxy-1-naphthyl)dimeth-
ylsulfonium hexafluoroantimonate and (4-hydroxy-1-naph-
thyl)dimethylsulfonium trifluoromethanesulfonate.

Examples of the halogenated alkyltriazine compound
include 2-methyl-4,6-bis(trichloromethyl)-1,3,5-triazine,
2,4,6-tris(trichloromethyl)-1,3,5-triazine, 2-phenyl-4,6-bis
(trichloromethyl)-1,3,5-triazine, 2-(4-chlorophenyl)-4,6-bis
(trichloromethyl)-1,3,5-triazine, 2-(4-methoxyphenyl)-4,6-
bis(trichloromethyl)-1,3,5-triazine, 2-(4-methoxy-1-
naphthyl)-4,6-bis(trichloromethyl)-1,3,5-triazine, 2-(benzo
[d][1,3]dioxoran-5-yl)-4,6-bis(trichloromethyl)-1,3,5-triazi
ne, 2-(4-methoxystyryl)-4,6-bis(trichloromethyl)-1,3,5-tri-
azine, 2-(3,4,5-trimethoxystyryl)-4,6-bis(trichloromethyl)-
1,3,5-triazine, 2-(3,4-dimethoxystyryl)-4,6-bis(trichlorom-
ethyl)-1,3,5-triazine, 2-(2,4-methoxystyryl)-4,6-bis
(trichloromethyl)-1,3,5-triazine, 2-(2-methoxystyryl)-4,6-
bis(trichloromethyl)-1,3,5-triazine, 2-(4-butoxystyryl)-4,6-
bis(trichloromethyl)-1,3,5-triazine and 2-(4-
pentyloxystyryl)-4,6-bis(trichloromethyl)-1,3,5-triazine.

Examples of the sulfonate compound include 1-benzoyl-
1-phenylmethyl p-toluenesulfonate (generally called "ben-
zoin tosylate"), 2-benzoyl-2-hydroxy-2-phenylethyl p-tolu-
enesulfonate (generally called "α-methylolbenzoin
tosylate"), 1,2,3-benzene-tri-yl tris(methanesulfonate), 2,6-
dinitrobenzyl p-toluenesulfonate, 2-nitrobenzyl p-toluene-
sulfonate and 4-nitrobenzyl p-toluenesulfonate.

Examples of the disulfone compound include diphenyl
disulfone and di(p-tolyl)disulfone.

Examples of the diazomethane compound having a sulfo-
nyl group include bis(phenylsulfonyl)diazomethane, bis(4-
dhlorophenylsulfonyl)diazomethane, bis(p-tolylsulfonyl)
diazomethane, bis(4-tert-butylphenylsulfonyl)
diazomethane, bis(2,4-xylylsulfonyl)diazomethane, bis
(cyclohexylsulfonyl)diazomethane and (benzoyl)
(phenylsulfonyl)diazomethane.

Examples of the imide compound having a sulfonyloxy
group include N-(phenylsulfonyloxy)succinimide, N-(trif-
luoromethylsulfonyloxy)succinimide, N-(trifluoromethyl-
sulfonyloxy)phthalimide, N-(trifluoromethylsulfonyloxy)-
5-norbornene-2,3-dicarboxylmide,
N-(trifluoromethylsulfonyloxy)naphthalimide and N-(10-
camphorsulfonyloxy)naphthalimide.

The acid generator may be used alone or a mixture of two
or more thereof may be used.

The present resist composition may further contain the
other polyhydric phenol compound in addition to the poly-
hydric phenol compound (I) and the acid generator.

As the other polyhydric phenol compound, a compound
which has at least one phenolic hydroxyl group and which is
soluble in alkali aqueous solution is exemplified.

Specific examples of the other polyhydric phenol com-
pound include the compound (III) and a compound repre-
sented by the following formula (V):

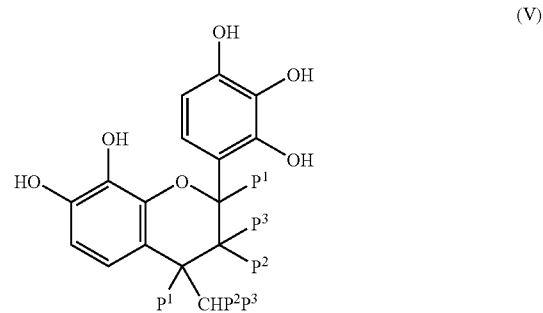

(V)

wherein $P^1$, $P^2$ and $P^3$ each independently represents a hydro-
gen atom, a C1-C4 alkyl group, a C2-C4 alkenyl group, a
C3-C8 cycloalkyl group, a C6-C12 aryl group or a C7-C12
aralkyl group.

Examples of the C1-C4 alkyl group include a methyl, ethyl,
n-propyl, n-butyl and isobutyl group. Examples of the C2-C4
alkenyl group include a vinyl, propenyl and 3-butenyl group.
Examples of the C3-C8 cycloalkyl group include a cyclopen-
tyl and cyclohexyl group. Examples of the C6-C12 aryl group
include a phenyl and tolyl group. Examples of the C7-C12
aralkyl group include a benzyl group. It is preferred that $P^1$, $P^1$
and $P^3$ each independently represent the hydrogen atom, the
methyl group or the ethyl group.

The compound represented by the formula (V) can be
produced according to the method described in U.S. Pat. No.
5,556,995.

The present resist composition also may contain at least
one resin containing a structural unit which has an acid-labile
group and which itself is insoluble or poorly soluble in an
aqueous alkali solution but becomes soluble in an aqueous
alkali solution by the action of an acid in addition to the
polyhydric phenol compound (I) and the acid generator.

The present resist composition also may contain the other
polyhydric phenol compound and at least one resin contain-
ing a structural unit which has an acid-labile group and which
itself is insoluble or poorly soluble in an aqueous alkali solu-
tion but becomes soluble in an aqueous alkali solution by the
action of an acid in addition to the polyhydric phenol com-
pound (I) and the acid generator.

The acid generated by irradiation to the acid generator
catalytically acts against acid-labile groups in the resin,
cleaves acid-labile groups, and the resin becomes soluble in
an alkali aqueous solution.

In the present specification, "—COOR" may be described
as "a structure having ester of carboxylic acid", and may also
be abbreviated as "ester group". Specifically, "—COOC
$(CH_3)_3$" may be described as "a structure having tert-butyl
ester of carboxylic acid", or be abbreviated as "tert-butyl ester
group".

Examples of the acid-labile group include a structure hav-
ing ester of carboxylic acid such as alkyl ester group in which
a carbon atom adjacent to the oxygen atom is quaternary
carbon atom, alicyclic ester group in which a carbon atom
adjacent to the oxygen atom is quaternary carbon atom, and a
lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit include a structure unit derived from an ester of acrylic acid, a structural unit derived from an ester of methacrylic acid, a structure unit derived from an ester of α-trifluoromethylacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid, from the ester of methacrylic acid and from the ester of α-trifluoromethylacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, a 2-alkyl-2-adamantyl α-trifluoromethylacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate, a 1-(1-adamantyl)-1-alkylalkyl α-chloroacrylate, a 2-alkyl-2-adamantyl α-trifluoromethylacrylate and a 1-(1-adamantyl)-1-alkylalkyl α-trifluoromethylacrylate.

Particularly when the 2-alkyl-2-adamantyl acrylate, the 2-alkyl-2-adamantyl methacrylate, the 2-alkyl-2-adamantyl α-trifluoromethylacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-n-butyl-2-adamantyl acrylate, 2-methyl-2-adamantyl α-trifluoromethylacrylate, 2-ethyl-2-adamantyl α-trifluoromethylacrylate, 2-isopropyl-2-adamantyl α-trifluoromethylacrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained.

In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide. The 2-alkyl-2-adamantyl α-trifluoromethylacrylate can be usually produced by reacting a 2-alkyl-2-adamantanol or a metal salt thereof with an α-trifluoromethylacrylic halide.

The resin can also contain other structural unit or units derived from an acid-stable monomer in addition to the above-mentioned structural units having the acid-labile group. Herein, the "structural unit derived from an acid-stable monomer" means "a structural unit not dissociated by an acid generated".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;
a structural unit derived from β-methacryloyloxy-γ-butyrolactone;
a structural unit represented by the formula (X):

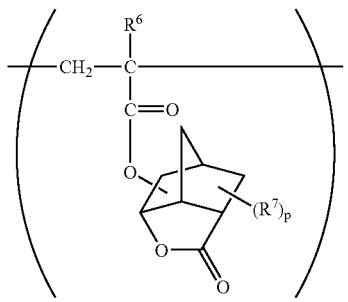

(X)

wherein $R^6$ represents a hydrogen atom or a methyl group, $R^7$ represents a methyl group, a trifluoromethyl group or a halogen atom, p represents an integer of 0 to 3, and when p represents 2 or 3, $R^7$s may be the same or different each other;
a structural unit represented by the formula ($X^1$):

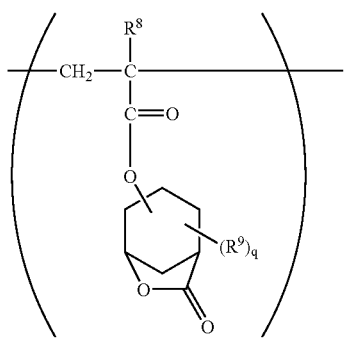

(XI)

wherein $R^8$ represents a hydrogen atom or a methyl group, $R^9$ represents a methyl group, a trifluoromethyl group or a halogen atom, q represents an integer of 0 to 3, and when q represents 2 or 3, $R^9$s may be the same or different each other;
a structural unit derived from p-hydroxystyrene;
a structural unit derived from m-hydroxystyrene;
a structural unit derived from an alicyclic compound having an olefinic double bond such as a structural unit represented by the formula (XII):

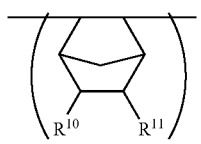

(XII)

wherein $R^{10}$ and $R^{11}$ each independently represents a hydrogen atom, a C1-C3 alkyl group, a C1-C3 hydroxyalkyl group, a carboxyl group, a cyano group or a —COOU group in which U represents an alcohol residue, or $R^{10}$ and $R^{11}$ can be bonded together to form a carboxylic anhydride residue represented by —C(=O)OC(=O)—;

a structural unit derived from an aliphatic unsaturated dicarboxylic anhydride such as a structural unit represented by the formula (XIII):

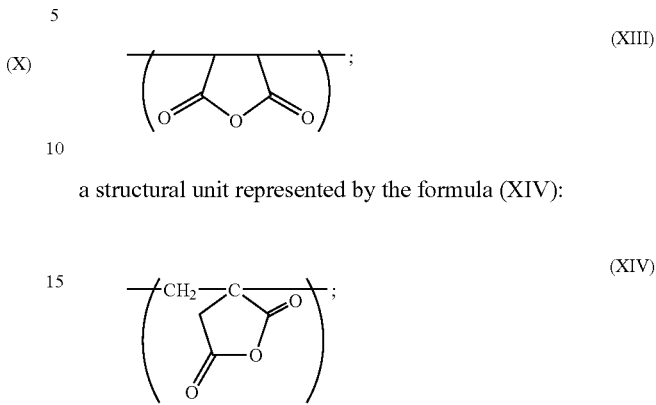

(XIII)

a structural unit represented by the formula (XIV):

(XIV)

and the like.

Particularly, the resin having further at least one structural unit selected from the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (X) and the structural unit represented by the formula ($X^1$) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting the corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (X) and (XI), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

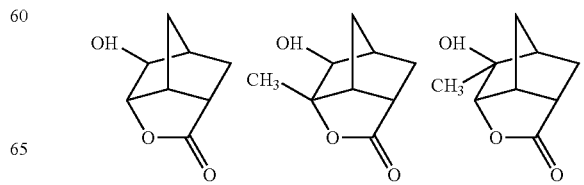

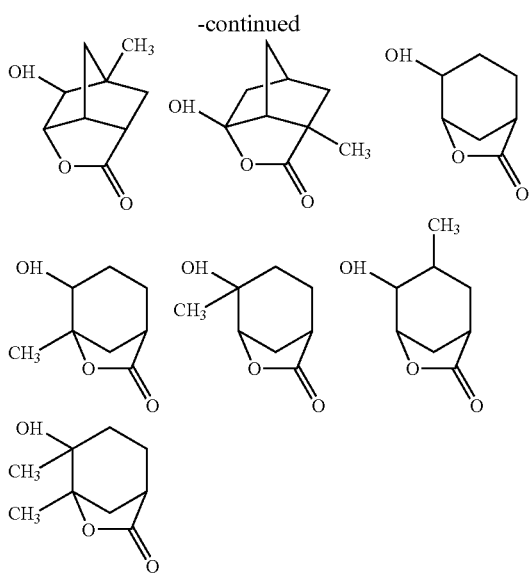

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, α-acryloyloxy-γ-butyrolactone, β-methacryloyloxy-γ-butyrolactone and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (XII). The structural unit derived from maleic anhydride and from itaconic anhydride which are the structural unit derived from aliphatic unsaturated dicarboxylic anhydrides are formed by opening of their double bonds, and can be represented by the above-mentioned formula (XIII) and the formula (XIV), respectively.

In $R^{10}$ and $R^{11}$, examples of the C1-C3 alkyl group include a methyl, ethyl, and n-propyl group, and examples of the C1-C3 hydroxyalkyl group include a hydroxymethyl and 2-hydroxyethyl group.

In $R^{10}$ and $R^{11}$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (XII) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (XII) is a structural unit having the acid-labile group even if it has the norbornane structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, and the like.

The resin preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

The resin can be produced, for example, by conducting polymerization reaction of the corresponding monomer or monomers. The resin can also be produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on molar amount of all monomer or oligomer.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After competition of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

It is preferable that the present resist composition contains the polyhydric phenol compound (I) in an amount of about 65 to 99.9% by weight and the acid generator in an amount of 0.1 to 35% by weight on the total amount of the polyhydric phenol compound (I), the acid generator and the resin component. In the present specification, "the resin component" means the component or components except the polyhydric phenol compound (I), the acid generator and a solvent in the present resist composition.

In the present resist composition, the amount of the polyhydric phenol compound (I) is preferably 10 to 100% by weight, more preferably 20 to 100% by weight, and especially preferably 30 to 100% by weight based on the total amount of the resin component and the polyhydric phenol compound (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

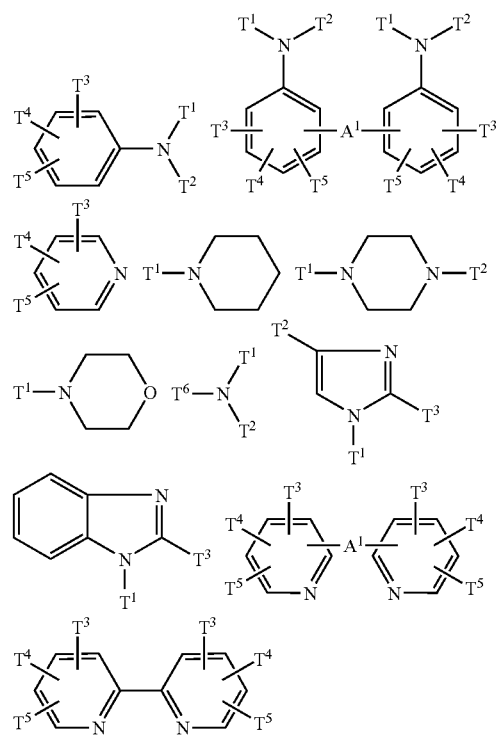

wherein $T^1$ and $T^2$ independently represent a hydrogen atom, an alkyl group, a cycloalkyl group or an aryl group, and the alkyl, cycloalkyl and aryl groups may be substituted with at least one group selected from a hydroxyl group, an amino group which may be substituted with a C1-C4 alkyl group and a C1-C6 alkoxy group which may be substituted with a C1-C6 alkoxy group, $T^3$ and $T^4$ independently represent a hydrogen atom, an alkyl group, a cycloalkyl group, an aryl group or an alkoxy group, and the alkyl, cycloalkyl, aryl and alkoxy groups may be substituted with at least one group selected from a hydroxyl group, an amino group which may be substituted with a C1-C4 alkyl group and a C1-C6 alkoxy group, or $T^3$ and $T^4$ bond together with the carbon atoms to which they bond to form an aromatic ring, $T^5$ represent a hydrogen atom, an alkyl group, a cycloalkyl group, an aryl group, an alkoxy group or a nitro group, and the alkyl, cycloalkyl, aryl and alkoxy groups may be substituted with at least one group selected from a hydroxyl group, an amino group which may be substituted with a C1-C4 alkyl group and a C1-C6 alkoxy group, $T^6$ represents an alkyl or cycloalkyl group, and the alkyl and cycloalkyl groups may be substituted with at least one group selected from a hydroxyl group, an amino group which may be substituted with a C1-C4 alkyl group and a C1-C6 alkoxy group, and $A^1$ represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

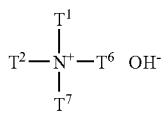

wherein $T^1$, $T^2$ and $T^6$ are the same as defined above, and $T^7$ represents a hydrogen atom, an alkyl group, a cycloalkyl group or an aryl group, and the alkyl and cycloalkyl groups may be substituted with at least one group selected from a hydroxyl group, an amino group which may be substituted with a C1-C4 alkyl group and a C1-C6 alkoxy group, and the aryl group may be substituted with at least one group selected from a hydroxyl group, an amino group which may be substituted with a C1-C4 alkyl group, a C1-C6 alkoxy group and a C1-C4 perfluoroalkyl group.

The alkyl group in $T^1$, $T^2$, $T^3$, $T^4$, $T^5$, $T^6$ and $T^7$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $T^1$, $T^2$, $T^3$, $T^4$, $T^5$, $T^6$ and $T^7$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $T^1$, $T^2$, $T^3$, $T^4$ and $T^5$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The aryl group in $T^7$ preferably has about 6 to 10 carbon atoms. Specific examples of the aryl group which may be substituted with at least one group selected from a hydroxyl group, an amino group which may be substituted with a C1-C4 alkyl group, a C1-C6 alkoxy group and a C1-C4 perfluoroalkyl group include a phenyl, naphthyl and 3-trifluoromethylphenyl group.

The alkoxy group in $T^3$, $T^4$ and $T^5$ preferably has about 1 to 6 carbon atoms and specific examples thereof include a methoxy, ethoxy, n-propoxy, isopropoxy, n-butoxy, tert-butoxy, n-pentyloxy, n-hexyloxy group.

The alkylene and alkenylene groups in $A^1$ preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylendiamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopuropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

The amount of the quencher is usually 0.001 to 10 parts by weight, preferably 0.01 to 5 parts by weight relative to 100 parts by weight of the polyhydric phenol compound (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted.

EXAMPLE 1

10 Parts of 2,6-bis[4-hydroxy-3-(2-hydroxy-5-methylbenzyl)-2,5-dimethylbenzyl]-4-methylphenol (hereinafter, simply referred to as B1) was dissolved in 100 parts of N,N-dimethylformamide. To the resultant solution, 6.8 parts of potassium carbonate was added. To the mixture obtained, a solution obtained by mixing 7.9 parts of 2-methyl-2-adamantyl chloroacetate with 40 parts of N,N-dimethylformamide was added dropwise below 50° C. 0.6 Part of potassium iodide was added to the mixture obtained and the resultant mixture was stirred at 50° C. for 5 hours. The reaction mixture was cooled, diluted with 1% aqueous oxalic acid solution and then extracted with ethyl acetate. The organic layer obtained was mixed with magnesium sulfate and activated carbon to dry and decolorize. The mixture obtained was filtrated and the filtrate obtained was concentrated to obtain 15.3 parts of brown solid, which is called as A1. Yield: 92%.

A1 was analyzed by liquid chromatography to find that three polyhydric phenol compounds represented by the following formulae (I) to (3):

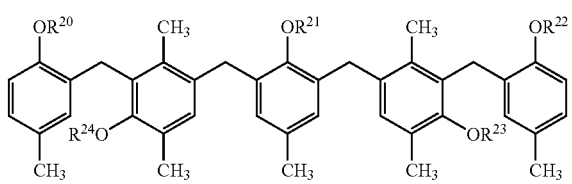
(1)

wherein any one of $R^{20}$, $R^{21}$, $R^{22}$, $R^{23}$ and $R^{24}$ is the following group:

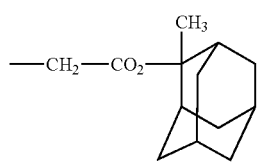

and the other four groups are hydrogen atoms (hereinafter, simply referred to as COMPOUND (1)),

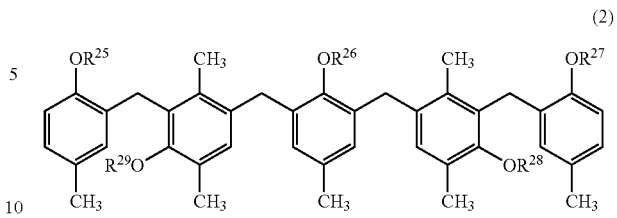
(2)

wherein any two of $R^{25}$, $R^{26}$, $R^{27}$, $R^{28}$ and $R^{29}$ are the following groups:

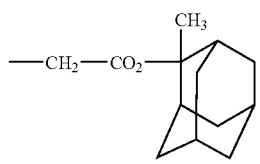

and the other three groups are hydrogen atoms (hereinafter, simply referred to as COMPOUND (2)),

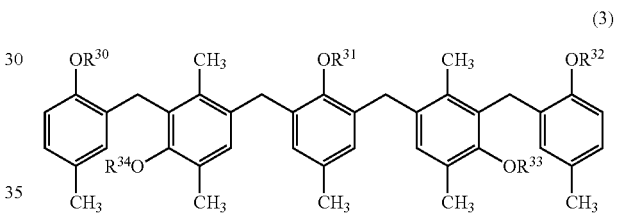
(3)

wherein any three of $R^{30}$, $R^{31}$, $R^{32}$, $R^{33}$ and $R^{34}$ are the following groups:

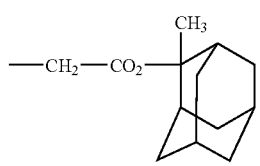

and the other two groups are hydrogen atoms (hereinafter, simply referred to as COMPOUND (3)) were contained in A1.

The content ratio of COMPOUND (1), COMPOUND (2) and COMPOUND (3) in A1 is shown in Table 1-1. Herein, "the content ratio" means a ratio of values of each compounds calculated by a liquid chromatography area percentage method.

Liquid chromatography mass spectroscopy;
COMPOUND (1): $[M+K]^+=861.4$ ($M^+=822.45$)
COMPOUND (2): $[M+K]^+=1067.4$ ($M^+=1028.58$)
COMPOUND (3): $[M+K]^+=1273.6$ ($M^+=1234.71$)

EXAMPLES 2 to 5

According to a similar manner as that of Example 1, the reactions were conducted to obtain solids containing COM- POUNDS (1) to (3) except that the molar amount of 2-methyl-2-adamantyl chloroacetate was changed as shown in Table 1-1.

The results are shown in Table 1-1.

Herein, molar ratio of 2-methyl-2-adamantyl chloroacetate was calculated by dividing molar amount of 2-methyl-2-adamantyl chloroacetate by molar amount of B1. "Content Ratio" means a ratio of values of each compound calculated by a liquid chromatography area percentage method.

The solid obtained in Example 2 is called as A2 and the solid obtained in Example 5 is called as A3.

TABLE 1-1

| Ex. No. | Molar ratio of 2-methyl-2-adamantyl chloroacetate | Content Ratio (%) | | |
|---|---|---|---|---|
| | | B1 | COMPOUND (1) | COMPOUND (2) | COMPOUND (3) |
| 1 | 2.0 | 0 | 4 | 92 | 4 |
| 2 | 1.0 | 29 | 33 | 38 | 0 |
| 3 | 1.5 | 4 | 29 | 67 | 0 |
| 4 | 1.8 | 1 | 21 | 78 | 0 |
| 5 | 3.0 | 0 | 1 | 56 | 43 |

EXAMPLE 6

50.8 Parts of B1 was dissolved in 435 parts of N,N-dimethylformamide. To the resultant solution, 32.88 parts of potassium carbonate was added. To the mixture obtained, a solution obtained by mixing 43.5 parts of 2-ethyl-2-adamantyl chloroacetate with 218 parts of N,N-dimethylformamide was added dropwise below 50° C. 2.63 Part of potassium iodide was added to the mixture obtained and the resultant mixture was stirred at 50° C. for 5 hours. The reaction mixture was cooled, diluted with 5% aqueous oxalic acid solution and then extracted with ethyl acetate. The organic layer obtained was washed with water and mixed with magnesium sulfate and activated carbon to dry and decolorize. The mixture obtained was filtrated and the filtrate obtained was concentrated to obtain 65.76 parts of brown solid, which is called as A4. Yield: 76%.

A4 was analyzed by liquid chromatography to find that three polyhydric phenol compounds represented by the following formulae (4) to (6):

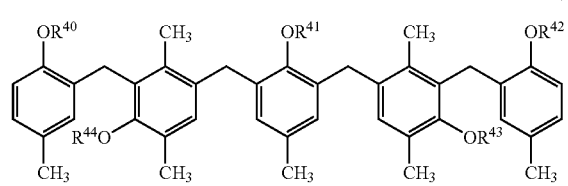

(4)

wherein any one of $R^{40}$, $R^{41}$, $R^{42}$, $R^{43}$ and $R^{44}$ is the following group:

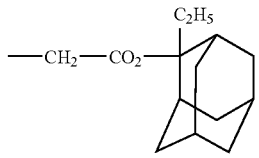

and the other four groups are hydrogen atoms (hereinafter, simply referred to as COMPOUND (4)),

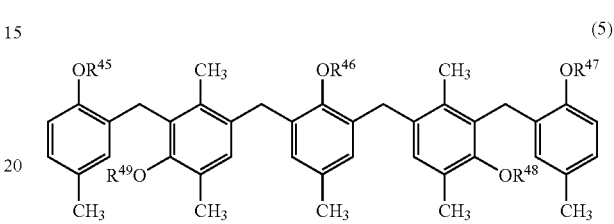

(5)

wherein any two of $R^{45}$, $R^{46}$, $R^{47}$, $R^{48}$ and $R^{49}$ are the following groups:

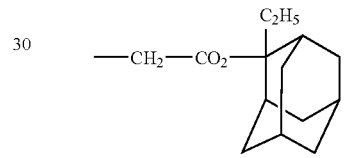

and the other three groups are hydrogen atoms (hereinafter, simply referred to as COMPOUND (5)),

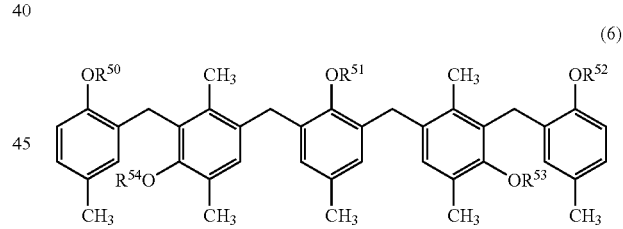

(6)

wherein any three of $R^{50}$, $R^{51}$, $R^{52}$, $R^{53}$ and $R^{54}$ are the following groups:

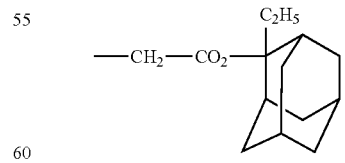

and the other two groups are hydrogen atoms (hereinafter, simply referred to as COMPOUND (6)) were contained in A4.

The content ratio of COMPOUND (4), COMPOUND (5) and COMPOUND (6) in A4 is shown in Table 1-2. Herein, "the content ratio" means a ratio of values of each compounds calculated by a liquid chromatography area percentage method.

Liquid chromatography mass spectroscopy;
COMPOUND (4): [M+K]$^+$=875.3 (M$^+$=836.47)
COMPOUND (5): [M+K]$^+$=1095.4 (M$^+$=1056.61)
COMPOUND (6): [M+K]$^+$=1315.5 (M$^+$=1276.76)

EXAMPLE 7

According to a similar manner as that of Example 6, the reaction was conducted to obtain the solid containing COMPOUNDS (4) to (5) except that the molar amount of 2-ethyl-2-adamantyl chloroacetate was changed as shown in Table 1-2.

The result is shown in Table 1-2.

Herein, molar ratio of 2-ethyl-2-adamantyl chloroacetate was calculated by dividing molar amount of 2-ethyl-2-adamantyl chloroacetate by molar amount of B1. "Content Ratio" means a ratio of values of each compound calculated by a liquid chromatography area percentage method.

TABLE 1-2

| Ex. No. | Molar ratio of 2-ethyl-2-adamantyl chloroacetate | Content Ratio (%) | | | |
|---|---|---|---|---|---|
| | | B1 | COMPOUND (4) | COMPOUND (5) | COMPOUND (6) |
| 6 | 2.0 | 0 | 12 | 84 | 4 |
| 7 | 1.0 | 23 | 52 | 25 | 0 |

REFERENCE EXAMPLE 1

According to the method described in JP 2003-107708A1, a copolymer of 2-ethyl-2-adamantyl methacrylate and p-hydroxystyrene (2-ethyl-2-adamantyl methacrylate/p-hydroxystyrene ratio=20/80), which is called as C1, a copolymer of 2-ethyl-2-adamantyl methacrylate and p-hydroxystyrene (2-ethyl-2-adamantyl methacrylate/p-hydroxystyrene ratio=30/70), which is called as C2, and a copolymer of 2-methyl-2-adamantyl methacrylate and p-hydroxystyrene (2-methyl-2-adamantyl methacrylate/p-hydroxystyrene ratio=30/70), which is called as C3, were synthesized.

REFERENCE EXAMPLE 2

According to the method described in U.S. Pat. No. 6,239,231 B1, a copolymer of 2-ethyl-2-adamantyl methacrylate, 3-hydroxy-1-adamantyl methacrylate and α-methacryloyl-γ-butyrolactone (2-ethyl-2-adamantyl methacrylate/3-hydroxy-1-adamantyl methacrylate/α-methacryloyl-γ-butyrolactone ratio=50/25/25), which is called as C4, was synthesized.

This copolymer C4 had the following structural units and the weight-average molecular weight thereof was about 9,200.

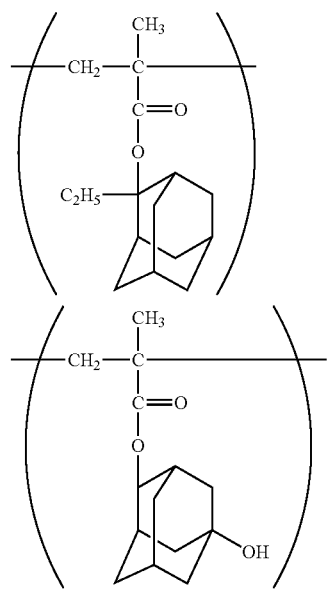

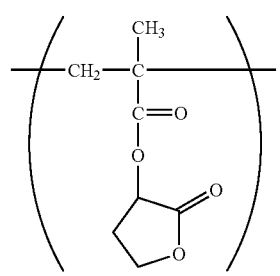

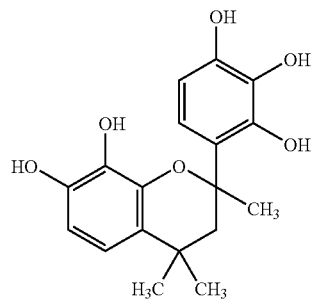

Reference Example 3

According to the method described in U.S. Pat. No. 5,556,995 B1, the polyhydric phenol compound represented by the following formula:

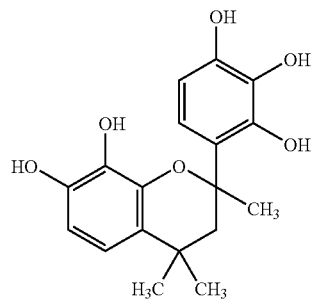

was synthesized from pyrogallol and acetone, which is called as B2.

Acid generators, quenchers and solvents used in following Examples are followings.

<Acid generator>

Acid generator S1: (4-methylphenyl)diphenylsulfonium nonafluorobutanesulfonate

Acid generator S2: triphenylsulfonium (1-adamantyl-methoxy)carbonyldifluoromethanesulfonate
Acid generator S3: triphenylsulfonium (4-oxo-1-adamantyloxy)carbonyldifluoromethanesulfonate
Acid generator S4: triphenylsulfonium (3-hydroxy-1-adamantyl)methoxycarbonyldifluoromethanesulfonate <Quencher>
Quencher Q1: 2,6-diisopropylaniline
Quencher Q2: tetrabutylammonium hydroxide <Solvent>

| Solvent Y: | propylene glycol monomethyl ether acetate | 180 parts |
| | 2-heptanone | 30 parts |
| | 1-methoxy-2-propanol | 40 parts |
| | γ-butyrolactone | 5 parts |

EXAMPLES 8 TO 29 AND COMPARATIVE EXAMPLES 1 TO 4

The following components were mixed to give a solution, and the solution was further filtrated through a fluorine resin filter having a pore diameter of 0.2 μm, to prepare resist liquid.

Compound (kind and amount are described in Tables 2-1 and 2-2)
Acid generator (kind and amount are described in Tables 2-1 and 2-2)
Quencher (kind and amount are described in Tables 2-1 and 2-2)
Solvent (kind are described in Tables 2-1 and 2-2)

TABLE 2-1

| Ex. No. | Compound (kind/amount (part)) | Acid generator (kind/amount (part)) | Quencher (kind/amount (part)) | Solvent | PB (° C.) | PEB (° C.) |
|---|---|---|---|---|---|---|
| Ex. 8 | A1/5 B1/5 | S1/0.8 | Q1/0.03 | Y | 110 | 105 |
| Ex. 9 | A1/5 B1/5 | S2/0.8 | Q1/0.03 | Y | 110 | 105 |
| Ex. 10 | A1/5 B1/5 | S3/0.8 | Q1/0.03 | Y | 110 | 105 |
| Ex. 11 | A1/5 B1/5 | S4/0.8 | Q1/0.03 | Y | 110 | 105 |
| Ex. 12 | A1/5 B1/5 | S3/3.0 | Q1/0.15 Q2/0.10 | Y | 110 | 95 |
| Ex. 13 | A1/7 B1/3 | S3/3.0 | Q1/0.15 Q2/0.10 | Y | 110 | 95 |
| Ex. 14 | A1/6 B1/2 B2/2 | S3/0.8 | Q1/0.18 | Y | 110 | 105 |
| Ex. 15 | A3/5 B1/5 | S3/3.0 | Q1/0.15 Q2/0.10 | Y | 110 | 95 |
| Ex. 16 | A4/5 B1/5 | S3/1.5 | Q1/0.05 Q2/0.05 | Y | 110 | 95 |
| Ex. 17 | A1/2.5 A4/2.5 B2/5 | S3/1.5 | Q1/0.01 | Y | 110 | 95 |
| Ex. 18 | A2/10 | S2/1.2 | Q1/0.01 | Y | 110 | 105 |
| Ex. 19 | A1/10 | S2/1.2 | Q1/0.075 | Y | 110 | 105 |
| Ex. 20 | A1/10 | S3/3.0 | Q1/0.01 | Y | 100 | 90 |
| Ex. 21 | A3/10 | S2/1.2 | Q1/0.01 | Y | 110 | 105 |
| Ex. 22 | A4/10 | S2/1.2 | Q1/0.01 | Y | 110 | 90 |
| Ex. 23 | A3/5 C4/5 | S1/1.2 | Q1/0.01 | Y | 110 | 105 |
| Ex. 24 | A3/5 C4/5 | S2/1.2 | Q1/0.01 | Y | 110 | 105 |
| Ex. 25 | A1/5 C2/5 | S2/1.2 | Q1/0.01 | Y | 110 | 105 |

TABLE 2-2

| Ex. No. | Compound (kind/amount (part)) | Acid generator (kind/amount (part)) | Quencher (kind/amount (part)) | Solvent | PB (° C.) | PEB (° C.) |
|---|---|---|---|---|---|---|
| Ex. 26 | A1/5 C3/5 | S1/1.2 | Q1/0.01 | Y | 110 | 110 |
| Ex. 27 | A1/5 C3/5 | S2/1.2 | Q1/0.01 | Y | 110 | 115 |

TABLE 2-2-continued

| Ex. No. | Compound (kind/amount (part)) | Acid generator (kind/amount (part)) | Quencher (kind/amount (part)) | Solvent | PB (° C.) | PEB (° C.) |
|---|---|---|---|---|---|---|
| Ex. 28 | A1/2.5 B1/2.5 C1/2.5 C2/2.5 | S3/1.5 | Q1/0.05 Q2/0.05 | Y | 110 | 95 |
| Ex. 29 | A1/5 C1/2.5 C2/2.5 | S3/1.5 | Q1/0.05 Q2/0.05 | Y | 110 | 100 |
| Comp. Ex. 1 | C1/5 C2/5 | S1/0.8 | Q1/0.018 | Y | 110 | 105 |
| Comp. Ex. 2 | C1/5 C2/5 | S2/0.8 | Q1/0.018 | Y | 110 | 105 |
| Comp. Ex. 3 | C1/5 C2/5 | S3/0.8 | Q1/0.018 | Y | 110 | 105 |
| Comp. Ex. 4 | C1/5 C2/5 | S4/0.8 | Q1/0.018 | Y | 110 | 105 |

Silicon wafers were each contacted with hexamethyldisilazane at 90° C. for 60 seconds and each of the resist liquids prepared as above was spin-coated over the silicon wafer to give a film thickness after drying of 0.12 μm. After application of each of the resist liquids, the silicon wafers thus coated with the respective resist liquids were each prebaked on a direct hotplate at a temperature shown in the column of "PB" in Table 2-1 or 2-2 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at a temperature shown in the column of "PEB" in Table 2-1 or 2-2 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 3.

Effective Sensitivity (ES): It is expressed as the amount of exposure that the line pattern and the space pattern become 1:1 after exposure through 0.10 μm line and space pattern mask and development.

Resolution: It is expressed as the minimum size of space pattern which gave the space pattern split by the line pattern at the exposure amount of the effective sensitivity.

Line Edge Roughness: when line edge roughness is very good, its evaluation is marked by "○", when line edge roughness is good, its evaluation is marked by "Δ", and when line edge roughness is bad, its evaluation is marked by "×".

TABLE 3

| Ex. No. | ES (μC) | Resolution (nm) | Line Edge Roughness |
|---|---|---|---|
| Ex. 8 | 10 | 120 | ○ |
| Ex. 9 | 8 | 90 | ○ |
| Ex. 10 | 16 | 70 | ○ |
| Ex. 11 | 12 | 70 | ○ |
| Ex. 12 | 24 | 90 | ○ |
| Ex. 13 | 24 | 80 | ○ |
| Ex. 14 | 12 | 80 | ○ |
| Ex. 15 | 24 | 90 | ○ |
| Ex. 16 | 17 | 50 | ○ |
| Ex. 17 | 24 | 80 | ○ |
| Ex. 18 | 11 | 90 | ○ |

TABLE 3-continued

| Ex. No. | ES (μC) | Resolution (nm) | Line Edge Roughness |
|---|---|---|---|
| Ex. 19 | 10 | 100 | ○ |
| Ex. 20 | 18 | 80 | ○ |
| Ex. 21 | 7 | 90 | ○ |
| Ex. 22 | 14 | 90 | ○ |
| Ex. 23 | 14 | 90 | ○ |
| Ex. 24 | 10 | 100 | ○ |
| Ex. 25 | 10 | 60 | ○ |
| Ex. 26 | 10 | 60 | ○ |
| Ex. 27 | 8 | 70 | ○ |
| Ex. 28 | 34 | 50 | ○ |
| Ex. 29 | 41 | 60 | ○ |
| Comp. Ex. 1 | 14 | 90 | X |
| Comp. Ex. 2 | 14 | 90 | X |
| Comp. Ex. 3 | 14 | 90 | X |
| Comp. Ex. 4 | 12 | 80 | X |

Apparent from the results shown in Table 3, the resist compositions obtained by Examples corresponding to the present invention show very good line edge roughness.

The present resist composition provides excellent resist pattern in line edge roughness and is suitable for extreme ultraviolet (EUV) lithography and electron lithography.

What is claimed is:

1. A polyhydric phenol compound represented by the formula (I):

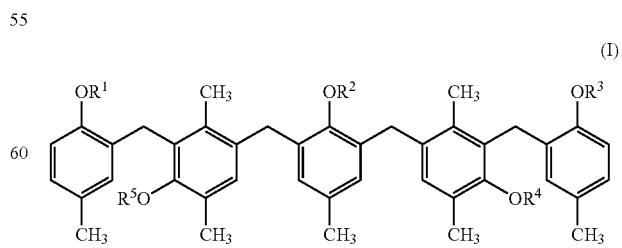

wherein at least one selected from $R^1$, $R^2$, $R^3$, $R^4$, and $R^5$ is a group represented by the formula (II):

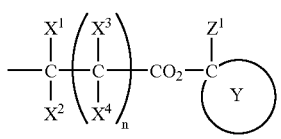

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms.

2. The polyhydric phenol compound according to claim 1, wherein $X^1$ and $X^2$ represent hydrogen atoms and n represents 0.

3. The polyhydric phenol compound according to claim 1, wherein the molecular weight of the polyhydric phenol compound represented by the formula (I) is 730 to 5000.

4. A chemically amplified resist composition comprising a polyhydric phenol compound represented by the formula (I):

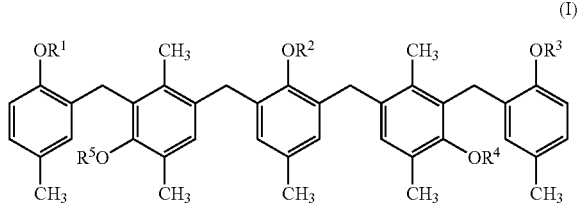

wherein at least one selected from $R^1$, $R^2$, $R^3$, $R^4$, and $R^5$ is a group represented by the formula (II):

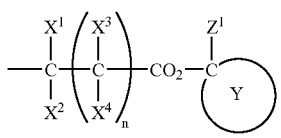

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms, and an acid generator.

5. The chemically amplified resist composition according to claim 4, wherein the composition contains at least two kinds of the polyhydric phenol compound represented by the formula (I).

6. The chemically amplified resist composition according to claim 4 or claim 5, wherein the composition further contains at least one compound selected from a compound represented by the formula (III):

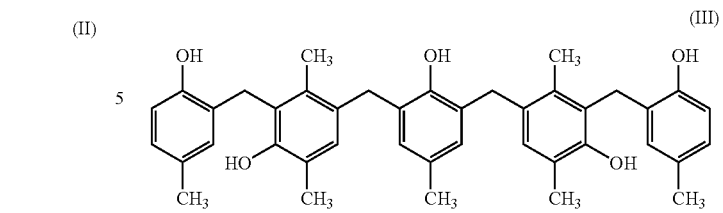

and a compound represented by the formula (V):

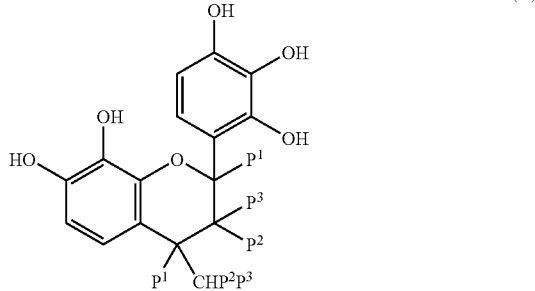

wherein $P^1$, $P^2$ and $P^3$ each independently represents a hydrogen atom, a C1-C4 alkyl group, a C2-C4 alkenyl group, a C3-C8 cycloalkyl group, a C6-C12 aryl group or a C7-C12 aralkyl group.

7. The chemically amplified resist composition according to claim 4 or claim 5, wherein the composition further contains a resin containing a structural unit which has an acid-labile group and which itself is insoluble or poorly soluble in an aqueous alkali solution but becomes soluble in an aqueous alkali solution by the action of an acid.

8. The chemically amplified resist composition according to claim 4 or claim 5, wherein the composition further contains a resin containing a structural unit which has an acid-labile group and which itself is insoluble or poorly soluble in an aqueous alkali solution but becomes soluble in an aqueous alkali solution by the action of an acid and at least one compound selected from a compound represented by the formula (III):

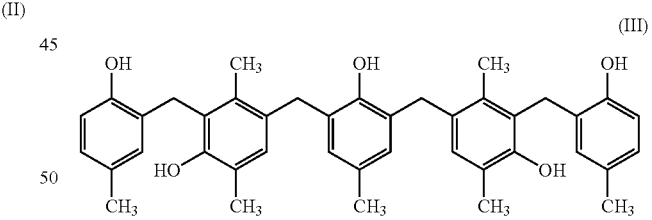

and a compound represented by the formula (V):

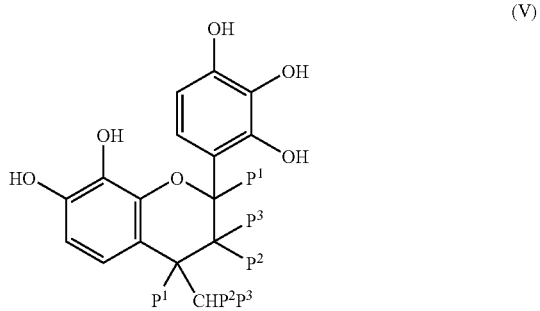

wherein $P^1$, $P^2$ and $P^3$ each independently represents a hydrogen atom, a C1-C4 alkyl group, a C2-C4 alkenyl group, a C3-C8 cycloalkyl group, a C6-C12 aryl group or a C7-C12 aralkyl group.

9. The chemically amplified resist composition according to claim 7, wherein the resin containing a structural unit which has an acid-labile group and which itself is insoluble or poorly soluble in an aqueous alkali solution but becomes soluble in an aqueous alkali solution by the action of an acid is a resin containing a structural unit derived from a 2-alkyl-2-adamantyl acrylate, a 2-alkyl-2-adamantyl methacrylate, a 2-alkyl-2-adamantyl α-chloroacrylate or a 2-alkyl-2-adamantyl α-trifluoromethylacrylate, and a structure unit derived from hydroxystyrene.

10. The chemically amplified resist composition according to claim 8, wherein the resin containing a structural unit which has an acid-labile group and which itself is insoluble or poorly soluble in an aqueous alkali solution but becomes soluble in an aqueous alkali solution by the action of an acid is a resin containing a structural unit derived from a 2-alkyl-2-adamantyl acrylate, a 2-alkyl-2-adamantyl methacrylate, a 2-alkyl-2-adamantyl α-chloroacrylate or a 2-alkyl-2-adamantyl α-trifluoromethylacrylate, and a structure unit derived from hydroxystyrene.

11. A process for production of a polyhydric phenol compound represented by the formula (I):

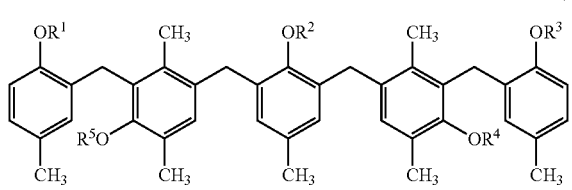

(I)

wherein at least one selected from $R^1$, $R^2$, $R^3$, $R^4$, and $R^5$ is a group represented by the formula (II):

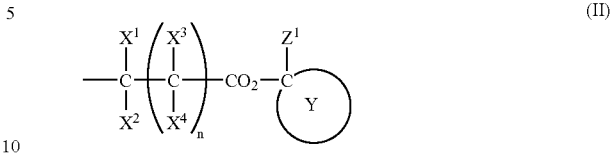

(II)

wherein $X^1$, $X^2$, $X^3$ and $X^4$ each independently represent a hydrogen atom or a C1-C4 alkyl group, n represents an integer of 0 to 3, $Z^1$ represents a C1-C6 alkyl group or a C3-C12 cycloalkyl group, and ring Y represents an alicyclic hydrocarbon group, and the others are hydrogen atoms, which comprises reacting a compound represented by the formula (III):

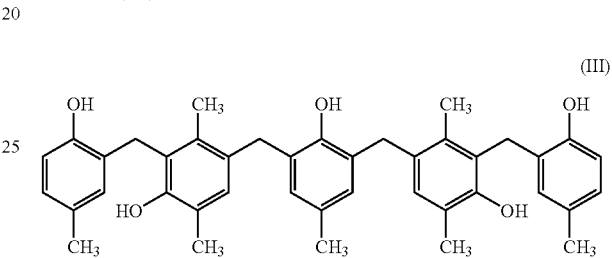

(III)

with a compound represented by the formula (IV):

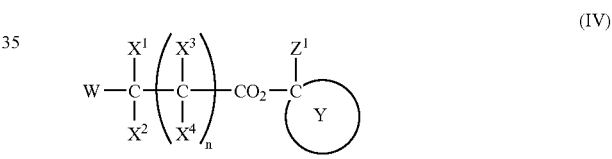

(IV)

wherein $X^1$, $X^2$, $X^3$, $X^4$, n, $Z^1$ and Y are the same as defined above, and W represents a chlorine atom, a bromine atom, an iodine atom, a methanesulfonyloxy group or a p-toluenesulfonyloxy group.

* * * * *